United States Patent
Joensuu et al.

(10) Patent No.: US 12,174,612 B2
(45) Date of Patent: Dec. 24, 2024

(54) ESTIMATING RISK LEVEL IN AN AQUEOUS PROCESS

(71) Applicant: KEMIRA OYJ, Helsinki (FI)

(72) Inventors: Iiris Joensuu, Espoo (FI); Marjatta Piironen, Espoo (FI)

(73) Assignee: Kemira Oyj, Helsinki (FI)

( * ) Notice: Subject to any disclaimer, the term of this patent is extended or adjusted under 35 U.S.C. 154(b) by 420 days.

(21) Appl. No.: 17/621,086

(22) PCT Filed: Jun. 17, 2020

(86) PCT No.: PCT/FI2020/050436
§ 371 (c)(1),
(2) Date: Dec. 20, 2021

(87) PCT Pub. No.: WO2020/254729
PCT Pub. Date: Dec. 24, 2020

(65) Prior Publication Data
US 2022/0326685 A1 Oct. 13, 2022

(30) Foreign Application Priority Data
Jun. 20, 2019 (FI) .................................. 20195550

(51) Int. Cl.
*G05B 19/4155* (2006.01)
*D21G 9/00* (2006.01)
(Continued)

(52) U.S. Cl.
CPC ....... *G05B 19/4155* (2013.01); *D21G 9/0018* (2013.01); *D21G 9/0027* (2013.01);
(Continued)

(58) Field of Classification Search
CPC ...... G05B 19/4155; G05B 2219/40006; D21G 9/0018; D21G 9/0027; D21G 9/0054;
(Continued)

(56) References Cited

U.S. PATENT DOCUMENTS

| 2009/0053224 A1* | 2/2009 | Smith | C07K 16/40 |
| | | | 424/139.1 |
| 2009/0084510 A1* | 4/2009 | Perry | G01N 33/343 |
| | | | 162/49 |

(Continued)

FOREIGN PATENT DOCUMENTS

| CL | 2016001183 A1 | 1/2017 |
| CL | 2018001664 A1 | 7/2018 |

(Continued)

OTHER PUBLICATIONS

Search Report issued on Jun. 27, 2023, by the Chilean Patent Office in corresponding Chilean Application No. 202103193, and an English Translation of the Search Report. (30 pages).

(Continued)

*Primary Examiner* — Ziaul Karim
(74) *Attorney, Agent, or Firm* — Espatent Oy

(57) ABSTRACT

Estimating or predicting runnability or end product quality risk level for a pulp or papermaking process is disclosed. The method includes measuring hydrophobicity values of samples originating from a same aqueous process stream. A hydrophobicity measurement signal is produced of measured hydrophobicity values as a function of time. A risk level is calculated for the process. At least one mathematical index is calculated based on the hydrophobicity measurement signal, and optionally based on the amount of particles in the sample, other property of the aqueous stream and/or production data. The mathematical index and optionally the amount of the particles, other property, and/or production data is used as a risk indicator input in the calculation. Based on the risk level calculated for the pulp or papermaking process, the runnability and/or end product quality risk level for the pulp or papermaking process is indicated.

30 Claims, 4 Drawing Sheets

(51) Int. Cl.
*G01N 21/64* (2006.01)
*G01N 33/34* (2006.01)

(52) U.S. Cl.
CPC ........... *D21G 9/0054* (2013.01); *G01N 21/64* (2013.01); *G01N 33/343* (2013.01); *G05B 2219/40006* (2013.01)

(58) Field of Classification Search
CPC .... D21G 9/0009; G01N 21/64; G01N 33/343; G01N 21/85; G01N 21/94
See application file for complete search history.

(56) References Cited

U.S. PATENT DOCUMENTS

| | | | | |
|---|---|---|---|---|
| 2011/0073263 | A1* | 3/2011 | Shevchenko | G01N 33/343 162/49 |
| 2012/0087917 | A1* | 4/2012 | Smith | A61P 35/04 435/235.1 |
| 2012/0258547 | A1* | 10/2012 | Von Drasek | G01N 21/6486 436/172 |
| 2019/0153675 | A1* | 5/2019 | Sharoyan | D21H 23/78 |

FOREIGN PATENT DOCUMENTS

| | | |
|---|---|---|
| FI | 20136172 A | 5/2015 |
| WO | 2007082376 A1 | 7/2007 |
| WO | 2008144383 A1 | 11/2008 |
| WO | 2015048241 A1 | 4/2015 |
| WO | 2015075306 A1 | 5/2015 |
| WO | 2015075319 A1 | 5/2015 |
| WO | 2017109287 A1 | 6/2017 |
| WO | 2019002699 A1 | 1/2019 |

OTHER PUBLICATIONS

International Search Report (PCT/ISA/210) and Written Opinion (PCT/ISA/237) mailed on Feb. 18, 2020, by the Finnish Patent Office as the International Searching Authority for International Application No. PCT/FI2020/050436.

* cited by examiner

ESTIMATING RISK LEVEL IN AN AQUEOUS PROCESS

FIELD OF THE INVENTION

The present invention relates to estimating risk level in an aqueous process, and more particularly to predicting risk level in a pulp, board or papermaking process or subprocess.

BACKGROUND ART

An example of an area where measurements of solid matter containing liquids is needed is forest industry, in which wood pulp samples or filtrates, such as wire water, white water, thickener filtrates or another similar pulp filtrate, or circulated water, need to be monitored in order to be able to control the overall process. E.g. in oil and mining industry processes and in water treatment industry, like water reuse, desalination processes and cooling water treatment, the liquids used often contain solid matter that need to be measured and monitored. On-line methods provide instant or almost instant information on the suspension.

Many such suspensions include particles, whose amount and size distribution have a considerable effect on upcoming process stages. E.g. agglomeration has, in fact, been shown to be the main threat for deposition and related running problems on paper machines. Liquids and filtrates in pulp industry also have a strong tendency to flocculate, which makes the analysis of the solid matter in liquid streams challenging.

The system may be based on field flow fractionation, where the fractionating is performed by conducting the sample to a disintegration channel that one or more depressions, and by applying a liquid flow having a non-constant temporal velocity profile through the disintegration channel. In this way, solid matter of the sample is gradually taken with the liquid flow from the depressions for providing sample fractions. This approach allows for measuring the particle size and/or mass distribution of a filtrate or a pulp sample.

Runnability problems such as paper defects in paper machines may be linked to strong agglomeration of hydrophobic particles in the wet end. Therefore, particle counts and hydrophobicity of the particles or particle populations, such as agglomerates, may need to be monitored.

SUMMARY

The following presents a simplified summary of features disclosed herein to provide a basic understanding of some exemplary aspects of the invention. This summary is not an extensive overview of the invention. It is not intended to identify key/critical elements of the invention or to delineate the scope of the invention. Its sole purpose is to present some concepts disclosed herein in a simplified form as a prelude to a more detailed description.

According to an aspect, there is provided the subject matter of the independent claims. Embodiments are defined in the dependent claims.

One or more examples of implementations are set forth in more detail in the accompanying drawings and the description below. Other features will be apparent from the description and drawings, and from the claims.

BRIEF DESCRIPTION OF THE DRAWINGS

In the following the invention will be described in greater detail by means of preferred embodiments with reference to the attached drawings, in which.

DETAILED DESCRIPTION OF EMBODIMENTS

Figure 1:
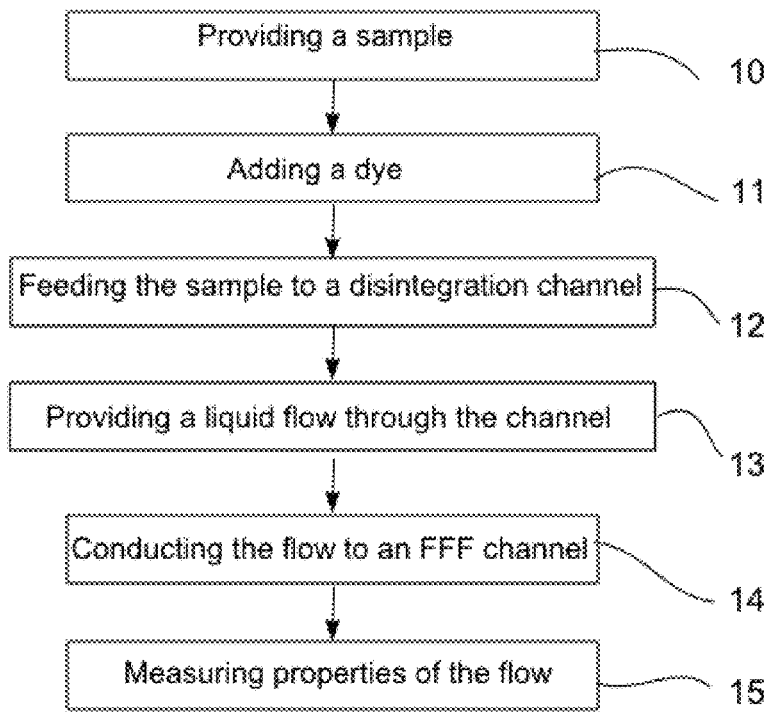
FIG. 1 illustrates an exemplary method.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising", "containing" and "including" should be understood as not limiting the described embodiments to consist of only those features that have been mentioned and such embodiments may contain also features/structures that have not been specifically mentioned.

In an embodiment, a method is disclosed for estimating and/or predicting a runnability risk level and/or end product quality risk level for a pulp, board or papermaking process. The method comprises providing samples from at least one aqueous stream of the pulp, board or papermaking process, and measuring hydrophobicity values of at least two samples originating from the same aqueous stream of the pulp, board or papermaking process. A hydrophobicity measurement signal of measured hydrophobicity values is produced as a function of time for said at least one aqueous stream. Said hydrophobicity measurement signal is processed to calculate a runnability risk level and/or end product quality risk level for the pulp, board or papermaking process, wherein the processing comprises calculating at least one mathematical index, based at least on the hydrophobicity measurement signal produced for said at least one aqueous stream, and optionally on the amount of particles in said at least one aqueous stream as a function of time, other property of said at least one aqueous stream as a function of time and/or production data as a function of time. The calculated mathematical index and optionally the amount of the particles in said at least one aqueous stream as a function of time, other property of said at least one aqueous stream as a function of time and/or production data as a function of time is used as a risk indicator input in the calculation of the runnability risk level and/or end product quality risk level. Based on the runnability risk level and/or end product quality risk level calculated for the pulp, board or papermaking process, the runnability risk level and/or the end product quality risk level for the pulp, board or papermaking process is indicated.

In another embodiment, a method is disclosed for estimating or predicting a runnability risk level and/or end product quality risk level for a pulp, board or papermaking process. The method comprises providing samples from at least one aqueous stream of the pulp, board or papermaking process, fractionating the samples into fractions based on mass and/or size of particles, and measuring hydrophobicity values of fractions of at least two samples originating from the same aqueous stream. A hydrophobicity measurement signal is produced of measured hydrophobicity values as a function of time for the fractions of said at least one aqueous stream. Said hydrophobicity measurement signal is processed to calculate a runnability risk level and/or end product quality risk level for the pulp, board or papermaking process, wherein the processing comprises calculating at least one mathematical index, based at least on the hydrophobicity measurement signal produced for the fractions of said at least one aqueous stream, and optionally on the amount of particles in said at least one aqueous stream as a function of time, other property of said at least one aqueous stream as a function of time and/or production data as a function of time. The calculated mathematical index and optionally the amount of the particles in said at least one aqueous stream as a function of time, other property of said at least one aqueous stream as a function of time and/or production data as a function of time is used as a risk indicator input in the calculation of the runnability risk level and/or end product quality risk level. Based on the runnability risk level and/or end product quality risk level calculated for the pulp, board or papermaking process, the runnability risk level and/or the end product quality risk level for the pulp, board or papermaking process is indicated.

In an embodiment, a hydrophobic dye may be added to the sample or fraction to stain the particles in the sample or fraction. A fluorescence intensity value may be measured by optical measurement for the sample or fraction to produce the hydrophobicity measurement signal. The produced measurement signal is representative of the hydrophobicity of the particles in the aqueous stream.

The calculated mathematical index may include a moving cumulative sum of the hydrophobicity, cumulative time of the hydrophobicity, moving median of the hydrophobicity, moving maximum of the hydrophobicity, and/or moving average of the hydrophobicity.

The calculated mathematical index may include a sum of the measured hydrophobicity values of the sample during a selected time period, an average of the measured hydrophobicity values of the sample during a selected time period, a median of the measured hydrophobicity values of the sample during a selected time period, and/or a maximum of the measured hydrophobicity values of the sample during a selected time period. The time period may be hours, days or a week.

The calculated mathematical index may include a difference between consecutive measured hydrophobicity values multiplied with a gain value. The gain value has a value>0. The gain value may be a specific constant value for a specific process stream. Examples of applicable gain values include 0.5, 1, 2, 10, etc.

The calculated mathematical index may include a difference between consecutive averages of the measured hydrophobicity values during selected time periods. For example, a change between successive hydrophobicity values, change in an hourly, daily and/or weekly level, i.e. the difference in consecutive hourly averages, the difference in consecutive daily averages, the difference in consecutive weekly averages may be utilized to monitor the direction and magnitude of the change. The sample may be fractionated into one or more of a fiber fraction, agglomerate fraction, floc fraction, fines fraction, and colloid fraction.

The calculated mathematical index may include the hydrophobicity measurement signal multiplied with a gain value. The gain value has a value>0. The gain value may be a specific constant value for a specific process stream. Examples of applicable gain values include 0.5, 1, 2, 10, etc.

In an embodiment, said other property of the aqueous stream is one or more of pH, conductivity, charge, temperature, COD (chemical oxygen demand) and particle size, consistency, ash consistency.

In an embodiment, the risk level may be calculated by inputting the risk indicator input to a risk indicator, the risk indicator being selected from one or more of a mathematical model, equation, statistical model, regression analysis based model, and/or rule based model. In an embodiment, the risk level may be calculated by inputting the risk indicator input to the risk indicator, wherein the risk indicator includes a threshold value for at least one risk indicator input and/or a weighting coefficient for at least one risk indicator input.

In an embodiment, the method comprises predicting runnability risks and/or end product quality risks caused by changes in process conditions of the pulp, board or papermaking process.

In an embodiment, based on the runnability risk level and/or the end product quality risk level, the concentration of hydrophobic contaminants in one or more aqueous streams of the pulp, board or papermaking process is controlled by manually and/or automatically adjusting the dosing of at least one chemical into the one or more aqueous streams of the pulp, board or papermaking process, and/or manually and/or automatically adjusting the dosing of washing water into the one or more aqueous streams of the pulp, board or papermaking process. Additionally/alternatively, fresh water use, opening the water circulation, machine washing, optimization of machine washing sequence, and/or improvements in pulp washing may be carried out or enabled based on the predicted risk level.

A risk indicator may be selected or created based on historical operational data on the pulp, board or papermaking process or subprocess, and/or the risk indicator may be process-specific or subprocess-specific.

The predicted runnability risk level and/or the predicted end product quality risk level may be output to the user.

The term end product as used herein may refer to paper, board, paperboard, pulp, pulp filtrate, and/or dried pulp.

The method may comprise indicating to the user, if the runnability risk level and/or the end product quality risk level exceeds a predefined value. An alarm may be raised, if the runnability risk level and/or the end product quality risk level exceeds a predefined value. At least two types or levels of alarms may be raised by an apparatus, in order to be received by the user. A first alarm level may be a yellow warning (indicating that the risk level is slightly increased), and a second alarm level may be a red alert (indicating that the risk level is high).

In an embodiment, the moving cumulative sum of the hydrophobicity is a daily cumulative sum for the hydrophobicity, the cumulative time of the hydrophobicity is a time interval during which the hydrophobicity exceeds a predefined hydrophobicity value, the moving median of the hydrophobicity is a daily median for the hydrophobicity, and/or the moving average of the hydrophobicity is a daily average for the hydrophobicity.

In an embodiment, the moving cumulative sum of the hydrophobicity is a cumulative sum of the measured hydrophobicity values of the sample during last 24 hours, the moving median of the measured hydrophobicity values of the sample during last 24 hours, and/or the moving average of the measured hydrophobicity values of the sample during last 24 hours. The time period for calculation of moving mathematical index may be hours (e.g. 8 h or 12 h), days, or a week.

In an embodiment, an apparatus is disclosed for estimating or predicting a runnability risk level and/or end product quality risk level for a pulp, board or papermaking process or subprocess, the apparatus comprising means for performing said method steps.

In an embodiment, the apparatus comprises means for obtaining samples from at least one aqueous stream of the pulp, board or papermaking process, measurement means for measuring hydrophobicity values of at least two samples originating from the same aqueous stream of the pulp, board or papermaking process, and processing means for producing a hydrophobicity measurement signal of measured hydrophobicity values as a function of time for said at least one aqueous stream. The processing means are configured to process said hydrophobicity measurement signal to calculate a runnability risk level and/or end product quality risk level risk level for the pulp, board or papermaking process, by calculating at least one mathematical index based on the hydrophobicity measurement signal produced for said at least one aqueous stream, and optionally the amount of particles in said at least one aqueous stream as a function of time, other property of said at least one aqueous stream as a function of time and/or production data as a function of time, wherein the processing means are configured to use the calculated mathematical index, and optionally the amount of the particles in said at least one aqueous stream as a function of time, other property of said at least one aqueous stream as a function of time and/or production data as a function of time, as a risk indicator input in the calculation of the risk level runnability risk level and/or end product quality risk level, and based on the risk level calculated for the pulp, board or papermaking process, indicate the runnability risk level and/or end product quality risk level for the pulp, board or papermaking process.

In an embodiment, the apparatus comprises means for obtaining a sample from at least one aqueous stream of the pulp, board or papermaking process, a fractionator for fractionating the sample into fractions based on mass and/or size of particles, measurement means for measuring hydrophobicity values of fractions of at least two samples originating from the same aqueous stream, and processing means for producing a hydrophobicity measurement signal of measured hydrophobicity values as a function of time for the fractions of said at least one aqueous stream. Said processing means are configured to process said hydrophobicity measurement signal to calculate a runnability risk level and/or end product quality risk level for the pulp, board or papermaking process, by calculating at least one mathematical index based at least on the hydrophobicity measurement signal produced for the fractions said at least one aqueous stream, and optionally on the amount of particles in said at least one aqueous stream as a function of time, other property of said at least one aqueous stream as a function of time and/or production data as a function of time, wherein the processing means are configured to use the calculated mathematical index, and optionally the amount of the particles in said at least one aqueous stream as a function of time, other property of said at least one aqueous stream as a function of time and/or production data as a function of time, as a risk indicator input in the calculation of the runnability risk level and/or end product quality risk level, and based on the risk level calculated for the pulp, board or papermaking process, indicate the runnability risk level and/or end product quality risk level for the pulp, board or papermaking process.

In an embodiment, the processing means are configured to calculate the risk level by inputting the risk indicator input to a risk indicator, the risk indicator being selected from one or more of a mathematical model, equation, statistical model, regression analysis based model, and/or rule based model.

In an embodiment, the processing means are configured to calculate the risk level by inputting the risk indicator input to a risk indicator, wherein the risk indicator includes a threshold value for at least one risk indicator input and/or a weighting coefficient for at least one risk indicator inputs.

In an embodiment, the apparatus is configured to predict runnability risks and/or end product quality risks caused by changes in process conditions of the pulp, board or papermaking process.

In an embodiment, the apparatus is configured to, based on the runnability risk level and/or the end product quality risk level, control the concentration (e.g. mg/liter) or the amount (e.g. relative number or amount of contaminants, e.g. between 0 to 100%) of hydrophobic contaminants in one or more aqueous streams by manually and/or automatically adjusting the dosing of at least one chemical into one or more aqueous streams, and/or manually and/or automatically adjusting the dosing of washing water into one or more aqueous streams. Additionally/alternatively, fresh water use, opening the water circulation, machine washing, optimization of machine washing sequence, and/or improvements in pulp washing may be carried out or enabled by the apparatus based on the predicted risk level.

In an embodiment, the apparatus is configured to select or create a risk indicator based on historical operational data on the pulp, board and/or papermaking process or subprocess, and/or a risk indicator is process-specific or subprocess-specific.

In an embodiment, the apparatus is configured to output to the user the runnability risk level and/or the end product quality risk level.

In an embodiment, the apparatus is configured to indicate to the user, if the runnability risk level and/or the end product quality risk level exceeds a predefined value.

In an embodiment, the apparatus is configured to raise an alarm, if the runnability risk level and/or the end product quality risk level exceeds a predefined value.

In an embodiment, the method and/or the apparatus is used in monitoring and controlling of chemical performance in a pulp, board or papermaking process. In an embodiment, the method and/or the apparatus is used in chemistry optimization or chemistry stabilization in a pulp, board or papermaking process. In an embodiment, the method and/or the apparatus is used in optimization and/or stabilization of wet end in paper making processes. In an embodiment, the method and/or the apparatus is used in reuse of water streams in a pulp, board or papermaking process.

In an embodiment, the method and/or the apparatus is used to measure hydrophobicity values of samples originating from at least two different aqueous streams of the pulp, board or papermaking process, produce a hydrophobicity measurement signal as a function of time for the difference between hydrophobicity values measured for said at least two aqueous streams, process said hydrophobicity measurement signal to calculate a runnability risk level and/or end product quality risk level for the pulp, board or papermaking process. The processing may comprise calculating at least one mathematical index, based at least on the hydrophobicity measurement signal produced for said at least two aqueous streams, and optionally on the amount of particles in said at least two aqueous streams as a function of time, other property of said at least two aqueous streams as a function of time and/or production data as a function of time. The calculated mathematical index and optionally the amount of the particles in said at least two aqueous streams as a function of time, other property of said at least two aqueous streams as a function of time and/or production data as a function of time may be used as a risk indicator input in the calculation of the runnability risk level and/or end product quality risk level; and based on the runnability risk level and/or end product quality risk level calculated for the pulp, board or papermaking process, indicating the runnability risk level and/or the end product quality risk level for the pulp, board or papermaking process. In this case, hydrophobicity values may be measured e.g. from headbox and wire water samples, and the difference between the hydrophobicity values is calculated to find out how much interfering substances is retained in the end product (i.e. paper, board or dried pulp). The hydrophobicity measurement signal is produced as a function of time for the difference between the hydrophobicity values measured for the at least two aqueous streams. The risk level may be calculated directly for the difference between the hydrophobicity values, or for the hydrophobicity measurement signal by using mathematical indices. Thus, in this case, hydrophobicity is measured at two different sampling points. For example, the measurements may be carried out before and after chemical addition, before and after a container, tank, tower and/or silo, before and after pH adjustment, and/or before and after filtering, and/or any other type of solid separation operation. The difference between the obtained hydrophobicity signals is calculated, and the risk level for this difference is obtained by means of the mathematical indices.

Chemicals that may be monitored and/or controlled by means of the method and apparatus include retention aid(s), deposit control chemical(s), sizing agent(s), fixing agent(s), dispersing agent(s), detackifier(s), passivator(s), polymer(s), enzyme(s), inorganic coagulant(s), and/or organic coagulant(s).

Examples of production data include production speed, machine speed, product grade, product grammage, type and share of incoming pulp including broke, total retention, ash retention, ash consistency in headbox and/or wire water, total consistency in headbox and/or wire water, chemical dosages in the paper machine, chemical dosages in the board machine, chemical dosages in the wet end and/or other parts of the pulp/paper/board making process, paper/board machine temperature.

Examples of aqueous streams to be analysed and/or controlled include process streams or subprocess streams such as pulp filtrate(s), incoming pulp, wire water, headbox stream (s), wet end stream(s), broke line stream(s), and/or white water. The aqueous streams may originate from different subprocesses of the pulp/paper/board making process.

In case the pulp process is integrated with the papermaking process, the term paper making process may refer to both the pulp process and the papermaking process. In case the pulp process is integrated with the board making process, the term board making process may refer to both the pulp process and the board making process.

In an embodiment, a runnability risk level and/or end product quality risk level is estimated and/or predicted for a pulp, board or papermaking subprocess, and the runnability and/or end product quality risk level estimated and/or predicted for the pulp, board or papermaking subprocess is used to estimate and/or predict the runnability risk level and/or the end product quality risk level for the (whole) pulp, board or papermaking process.

The present invention relates to an on-line system for continuous monitoring of hydrophobic particles in aqueous streams and pulp suspensions. The present invention involves means for interpreting the results and to extract risk indicator inputs based on particle counts and hydrophobicity of a sample. Pre-treatment and separation of samples in order to achieve the objectives is also disclosed.

The present invention is directed to a system and a method of analyzing a liquid sample containing particles of solid matter, where the analysis is done online by collecting a sample from a stream of liquid. A dye may be added to the sample to stain the particles contained therein. The sample may be fractionated, pretreated or untreated. Thus, the particles in the sample may be separated into different particle populations, the separation being carried out by fractionation, or by settling or centrifugation, e.g. according to the mass or size (or both) of the particles.

The sample may be conducted to a first flow chamber equipped with disintegration means, where a liquid flow of water is introduced with a velocity profile which causes fractioning of the sample particles into to one or several particle populations. Initially a low velocity is used, causing smaller or lighter particle populations to passes the disintegration means first, and by gradually, e.g. stepwise, increasing the liquid flow velocity according to the velocity profile, all particle populations pass the disintegration means at a retention time characteristic for the properties of each population. The particle populations flow into a second flow chamber having an essentially laminar flow, at which at least one physical or chemical property of the stained particles in a particle population is measured with optical instruments and/or detectors, in order to produce at least one measurement signal. The measurement signals are processed for each measured particle population to extract key variables descriptive of the measured properties, and to correlate measurements of individual populations to other parameters of the process and/or to key variables of the whole sample. The chemical or physical properties of the sample to be measured may be one or more of the following: concentration of particles, volume of particles, surface area of particles, particle size, turbidity, concentration of suspended solid, light absorbance, fluorescence, light scattering, and hydrophobicity.

The invention allows for measurement of particle counts and hydrophobicity for each population by using optical sensors/measurements like light scattering, particle counter, turbidity, absorbance, fluorescence, and suspended solids. This provides for the design of a robust and simple online system as each particle need not be the analyzed one by one.

The invention is also directed to the use of the method in a system for analyzing a liquid sample containing particles of solid matter.

FIG. 1 illustrates an exemplary method. Referring to FIG. 1, a sample may be provided 101 directly from a process and/or subprocess to be monitored or controlled. The sample may be a batch sample or "plug" of about 10 ml taken with automated sampling means. Next, in step 102, a hydrophobic dye such as Nile red may be used to stain the sample. In this optional pretreatment stage the particles are prepared for the measurement. The staining of the sample or particles of the sample is done before or in the disintegration channel, i.e. during an optional fractionation step 103. The amount of stain may be around 40 µl per millilitre of sample.

In the optional step 103, the sample is fed to a disintegration channel for fractionation. The sample is driven relatively fast to the channel so that it experiences rapid local accelerations which break potential flocks in the sample. The sample should however not be fed with a velocity making it pass the disintegration channel at once. A liquid flow, typically an aqueous flow, is conducted through the disintegration channel to a field flow fractionation channel (FFF) with essentially laminar flow properties. The overall dilution of the sample in water may be around 1:10-1:200, preferably around 1:50-1:70. In order to separate the smallest particles from the larger or heavier ones, the flow velocity is low at the beginning. In this way particle separation is achieved in channel with light particles passing the system first. In order to get heavier particles into the water flow, flow velocity is increased step by step. The velocity is thus increased to a level which catches even the heaviest (or at least all of interest) particles. As a consequence, the sample is effectively fractionated in the FFF channel. The flow velocity profiles may be optimized for different types of liquids, for example, one for paper machine white water samples and another for pulp samples.

The desired properties of the fractions or the sample are measured in step 104. Optical measurements may be performed in step 104, but there may also be alternative or additional measurement stages.

The disintegration and fractionation step 103 and typically also the measurement step 104, may occur at least partly simultaneously in a continuous configuration. However, it is also possible to recover the sample or fractions for subsequent separate measurements, if immediate on-line results are not needed.

Step 104 involves producing a hydrophobicity measurement signal of measured hydrophobicity values as a function of time.

In step 105, said hydrophobicity measurement signal is processed to calculate a risk level for the pulp, board or papermaking process and/or subprocess. The processing comprises calculating at least one mathematical index based on the hydrophobicity measurement signal, and optionally the amount of particles in the sample, other property of the sample and/or production data. The calculated mathematical index and optionally the amount of the particles in the sample and/or other property of the sample is used, in step 106, as a risk indicator input in the calculation of the risk level. Based on risk levels calculated for one or more pulp, board or papermaking subprocesses, a predicted runnability risk level and/or predicted end product quality risk level is estimated and indicated for the pulp, board or papermaking process. Said indicating may comprise outputting, in step 107, the predicted runnability risk level and/or the predicted end product quality risk level to the user. In step 108, based on the predicted runnability risk level and/or the predicted end product quality risk level, the concentration or amount of hydrophobic contaminants in the aqueous stream may be controlled by manually and/or automatically adjusting the dosing of at least one chemical into the aqueous stream, and/or by manually and/or automatically adjusting the dosing of pulp washing water into the aqueous stream.

The whole process described in FIG. 1 may take about 30 minutes, including fractionation and sample measuring and cleaning of the sampling system. There may be variation in the time cycle depending on the system and nature of the sample, for example, 2-180 minutes, or typically 5-50 minutes.

Figure 2:
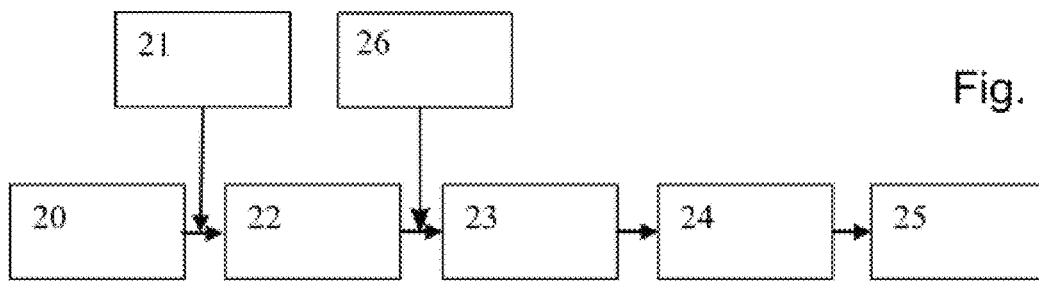
FIG. 2 illustrates an exemplary apparatus.

FIG. 2 illustrates an exemplary apparatus. Referring to FIG. 2, the apparatus may comprise a fractionator and a measurer unit 25 with one or more detectors. The fractionator may comprise a source 20 of fresh water and a sample-taking device 21. A pump 22 may be provided for driving the sample or water forward in the system using suitable valves (not shown). The pump 22 may be connected in forward direction to a first flow chamber, here a disintegration channel 23, and further to a second flow chamber, here a field flow fractionating (FFF) channel 24. A staining unit 26 with a dye reservoir (not shown) may be provided in order to feed the appropriate amount of dye to the sample before (or after) fractioning the particles into populations. The apparatus also includes a processing unit having e.g. a programmable logic (PLC) or industrial computer for automatic operation of the apparatus and data collection. The processing unit may also include a computer having appropriate software to carry out the processing of the measurement signals to extract the estimated/predicted risk levels which are the main deliverable of the apparatus. The computer may be included in the measurer unit 25, or be plugged into it as a separate computer, optionally for remote monitoring. An automatic cleaning system for the various liquid-carrying parts of the apparatus may also be provided.

The fractionator may also be of the type where particle separation into particle populations is based on particle settling, centrifugal separation or filtering according to the mass or size (or both) of the particles. Also, the sample may be fractionated as pretreated or untreated.

The present method is aimed for monitoring particles, e.g. colloids, stickies, wood pitch, white pitch, flocks, fines, fibers and/or agglomerated particles.

The measured quantities of the online system may be fluorescence intensity and turbidity, wherein the fluorescence intensity correlates directly with hydrophobicity of the sample or fractions when a hydrophobic dye like Nile red is added to the sample. Turbidity may be used for measuring particle concentrations. It should be noted that the particle size and/or particle volume also affects turbidity. Instead of turbidity, light scattering may be measured and used for determining particle concentrations.

Figure 3:
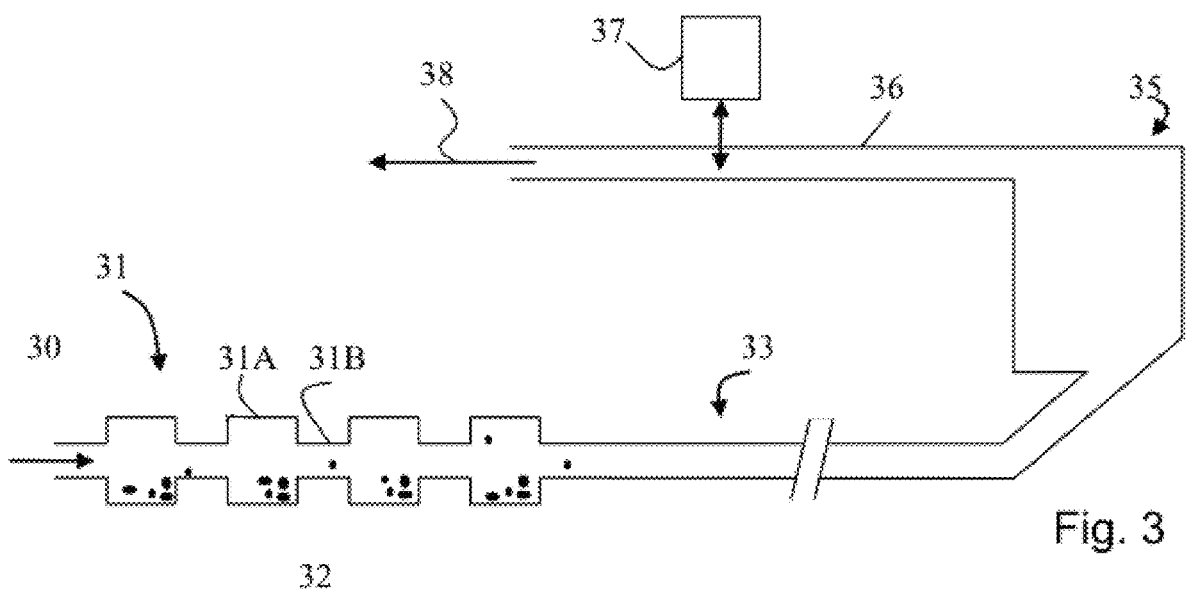
FIGS. 3 to 5 illustrate exemplary risk models.
Figure 4:
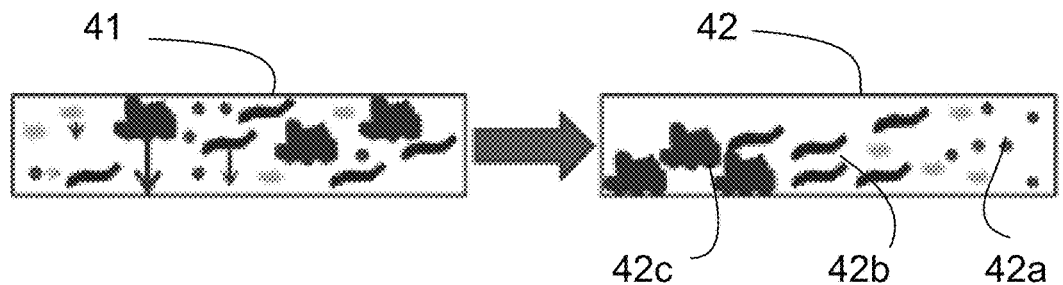
Figure 5:
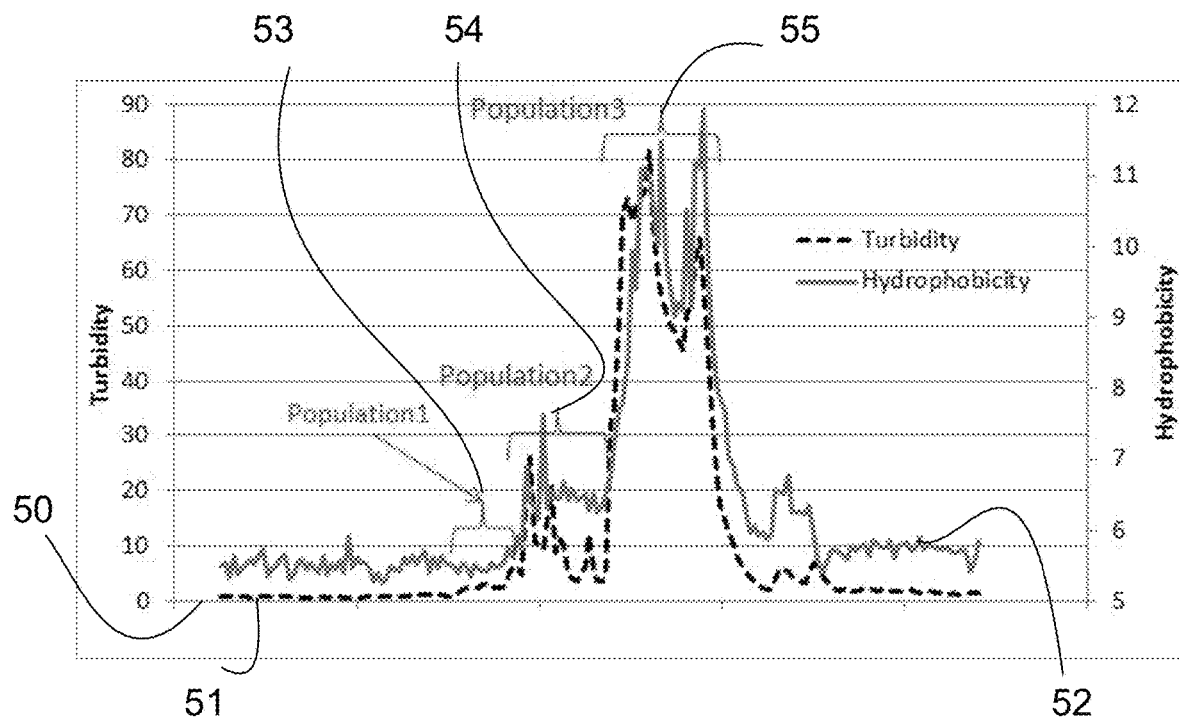

FIGS. 3, 4 and 5 show examples of a risk models where mathematical operations linked to the mathematical indexes, and rule-based risk indicators are used to predict or estimate the risk level in a paper making process. Risk level 0=low risk level. The higher the value of the risk level is, the higher is the risk for runnability problems. HF=hydrophobicity.

In FIG. 3, the risk level for defects in the end product is predicted/estimated. In FIG. 3, mathematical operations include weekly moving cumulative sum, and cumulative time when measured value exceeds a threshold value. Further in FIG. 3, rules for rule based risk indicators include:

risk indicator 1 (RI1)
  if cumulative sum<3000, then risk level is 0 (low),
  if cumulative sum 3000-3500, then risk level is 1 (medium),
  if cumulative sum 3500-4000, then risk level is 2 (high),
  if cumulative sum>4000, then risk level is 3 (very high);
risk indicator 2 (RI2, threshold 1=19.9)
  if cumulative time<1 hour, then risk level is 0 (low),
  if cumulative time 1-95 hours, then risk level is 1 (medium),
  if cumulative time>95 hours, then risk level is 2 (high);
risk indicator 3 (RI3, threshold 2=25)
  if cumulative time<1 hour, then risk level is 0 (low),
  if cumulative time 1-99 hours, then risk level is 1 (medium),
  if cumulative time>99 hours, then risk level is 2 (high).

Yet further in FIG. 3, the total risk level, i.e. the predicted/estimated risk level for defects in final product=RI1+RI2+RI3. In FIG. 3, threshold 1=19.9 (high hydrophobicity), and threshold 2=25 (extremely high hydrophobicity).

In FIG. 4, the risk level for chemistry related runnability issues is predicted/estimated. In FIG. 4, mathematical operations include daily moving average, cumulative time when daily moving average exceeds a threshold value, and daily moving cumulative sum. Further in FIG. 4, rules for rule based risk indicators include:

risk indicator 1 (RI1)

if cum time of HF (daily moving average>4) is 0, then the risk for runnability issues is low (risk level=0), if cumulative time of HF is more than 0 but less than 50 hours, then the risk for runnability issues has increased (risk level=1, medium), if cumulative time of HF is more than 50 hours, then the risk for runnability issues is very high (risk level=2, high);

risk indicator 2 (RI2)

if cumulative sum of HF<90, then the risk for runnability issues is low (risk level=0), if cumulative sum of HF is more than 90 but less than 125, then the risk for runnability issues increases (risk level=1, medium), if cumulative sum of HF is more than 125, then the risk for runnability issues is very high (risk level=2, high).

Yet further in FIG. 4, the total risk level, i.e. the predicted/estimated risk level for chemistry related runnability issues=RI1+RI2. In FIG. 4, threshold=4.

In FIG. 5, the risk level for dirt breaks is estimated. In FIG. 5, mathematical operations include daily moving cumulative sum (=hydrophobic load). Further in FIG. 5, rules for rule based risk indicators include:

rules for hydrophobic load if hydrophobic load is >450, then the risk for dirt breaks increases (risk level=2), if hydrophobic load is <450 and >350, then the risk for dirt breaks is medium (risk level=1), if hydrophobic load is <350, then the risk for dirt breaks is low (risk level=0);

rules for ash retention if ash retention is <55%, then the risk for dirt breaks increases (risk level=2), if ash retention is 60-65%, the risk for dirt breaks is medium (=1), if ash retention is >65%, the risk for dirt breaks is low (=0).

Yet further in FIG. 5, the total risk level, i.e. the estimated risk level for dirt breaks=0.3*R1+0.7*R2.

In a pulp/paper making process monitoring system, the following key variables may be extracted from measured data signals:

count(s) of particles: total count and count of each particle population from the turbidity signal;

size(s) of particles from the retention time of each particle populations in the system, i.e. the time when particles are exiting the fractionator;

particle size distribution from turbidity and retention time(s);

hydrophobicity of particles: total hydrophobicity and hydrophobicity of each particle population from the fluorescence signal;

hydrophobicity distribution of particles from fluorescence signal and retention time(s).

A specific software toolkit may be used for pretreatment of raw measurement data and calculation of key variables for the particle properties. The pretreatment may include filtering, averaging, derivation and/or baseline correction of the signals, or any other basic mathematical operations and/or the use of applicable functions to modify the raw measurement data. As an example of the procedure, the baseline may be removed from the raw measurement data of a fractionated sample, and the cumulative sums are calculated from the data. The cumulative sum of turbidity is correlated with the count of particles, and the cumulative sum of fluorescence is correlated with the hydrophobicity of the particles. Hydrophobicity and count for each particle population are derived from the data at certain time intervals. Each particle population has their own time interval in the second flow chamber. Total hydrophobicity and total count are derived from the whole data of fractionated samples. The turbidity, particle size and number in a sample population may be determined by measuring absolute values or relative values. If relative measurement is used, the processing means for processing the raw measurement data for each particle population is calibrated with regard to known samples.

In other words, key variables in a particle population are produced by means of calculating the cumulative sum, derivation, integral, mean, maximum and minimum values of the raw measurement data or pretreated measurement data, or by statistical operators yielding e.g. skewness, deviation, mode, median, quartales, range, variance, kurtosis, percentiles of the data, or by any other basic mathematical operations and/or the use of applicable functions to modify the key variables in order to attach physical/chemical properties to each population. The chemical or physical properties of the sample to be measured may be one or more of the following: concentration of particles, volume of particles, surface area of particles, particle size, turbidity, concentration of suspended solid, light absorbance, fluorescence, light scattering, and hydrophobicity. Raw measurement data or pretreated measurement data may be mapped on a coordinate system, in order to extract therefrom also other characteristics of the sample.

Optionally, a specific software toolkit contains means for calibration. Count of particles and/or size(s) of particles may be calibrated to SI-units using a suitable mathematical equation, e.g. first and/or second degree equations.

Optionally one or more key variables of individual populations or the whole sample are used for monitoring, controlling and/or optimization of a process (e.g. in a paper machine). For example, key variables may be used to monitor the running parameters and properties of a paper machine, including monitoring of agglomeration tendencies of particles in the process and, monitoring of chemical behavior in the process.

Optionally one or more key variables of individual populations or the whole sample are used for monitoring the performance of chemicals by controlling the chemicals (e.g. controlling the dosage of chemical) and optimization of chemical dosing or chemical program (type of chemicals, chemical dosages, dosing points of chemicals in the process).

An embodiment concerns sampling of liquids like aqueous suspensions or filtrates that contain solid matter in forest industry, oil and mining industry, as well as in water treatment, desalination or water reuse processes, and in subsequent measurement of the samples. In more detail, it relates to an on-line analysis method and system utilizing fractionation technology of a sample flow. The inventive technology is generic and can be widely applied in the pulp and paper industry, for example wet end monitoring, broke treatment, stickies control of recycled pulp and chemical/mechanical pulp treatment including bleaching and dry section of a paper, board or tissue machine. It may be used for online monitoring of particle populations like colloids, white pitch, wood pitch, stickies, fines, fillers, or agglomerates, and their hydrophobicity. The inventive online system enables real-time problem solving and optimization of chemistry in a pulp, paper or board mill.

An embodiment enables predicting runnability risk level e.g. for chemistry related runnability issues, machine fouling, process breaks such as chemistry related breaks, dirt breaks, deposit breaks, hole breaks, and/or increased amount of washing breaks.

An embodiment enables predicting end product quality risk level e.g. for chemistry related issues in the end product, defects in the end product, and/or different types of end product defects such as holes and/or spots. End product defects may be classified to different groups based on size and color.

A predictive system/method is thus provided, which indicates a risk level that a future runnability/product quality event is about to occur in the future. The predictive system/method is achieved by the calculation of the mathematical index (and optionally the amount of the particles in said at least one aqueous stream as a function of time, other property of said at least one aqueous stream as a function of time and/or production data as a function of time) which is used as a risk indicator input. The predictive system/method enables capturing a process trend to determine the runnability/product quality risk level. The tendency for runnability/product quality problems before they start to occur may thus be detected, and chemical dosing based on the predicted risk level may thus be scheduled. The predictive system/method enables providing a more accurate forecast on the state of the process, thereby suggesting actions to be taken to obtain an optimal outcome, e.g. to be able prevent the runnability/product quality problems e.g. by optimal chemical dosing. The chemical demand can be defined more accurately. Runnability/product quality problems can be eliminated or mitigated, wherein more product meeting the specifications is obtained and less waste material is produced. This also enables estimating/predicting how long the pulp, board or papermaking process can run until the runnability/product quality risk level is too high (exceeds certain predefined value), e.g. the runnability/product quality problems start to influence too much on the process runnability/product quality.

Example 1

Paper making process had deposit problems due to pitch from 10 June to 23 June. Hydrophobicity of particles in the wet end were measured from sample streams taken from the headbox and wire water.

Figure 6:
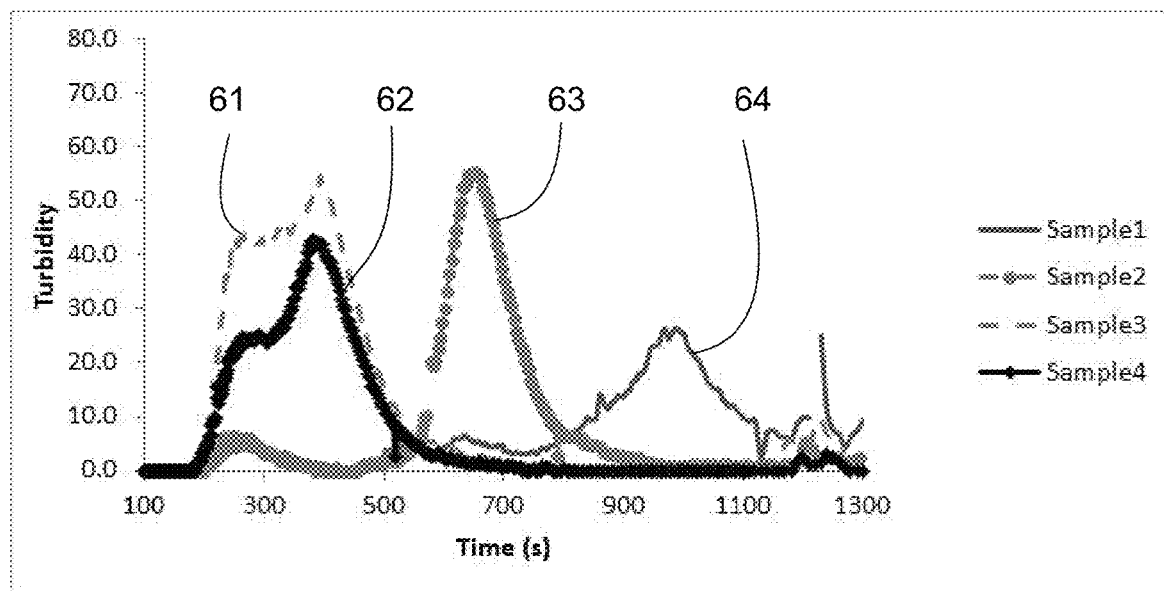
FIG. 6 shows an example of measured values and daily average for hydrophobicity of colloids in headbox.

FIG. 6 shows hydrophobicity of colloidal particles (wood pitch) as a function of time in the headbox sample, and a daily moving average of measured hydrophobicity values of the colloids.

Figure 7:
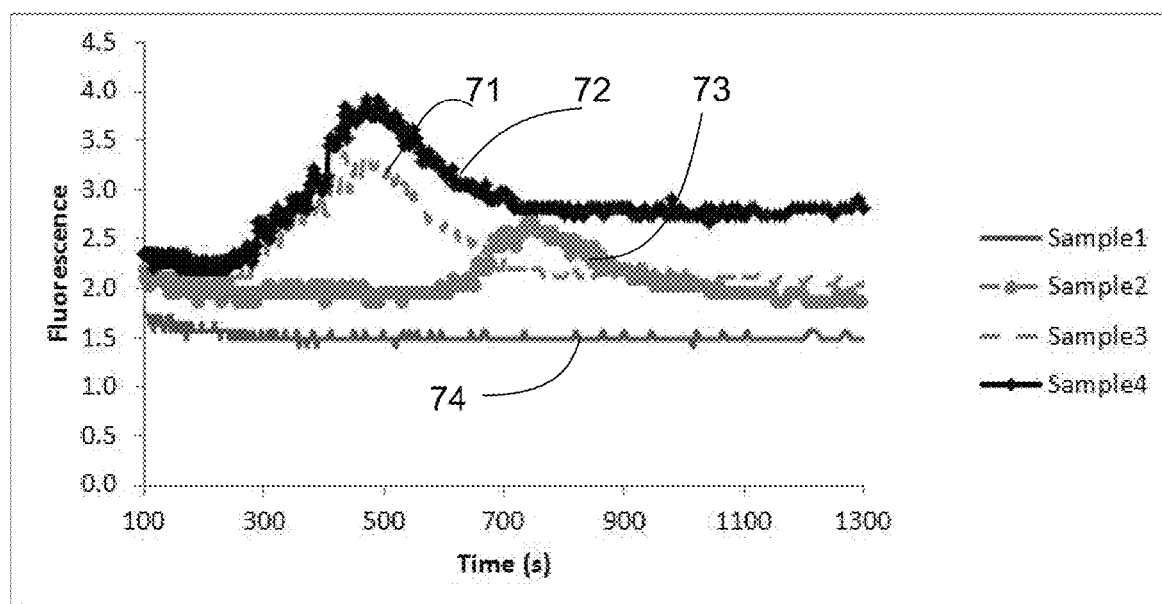
FIGS. 7 to 9 show examples of risk level calculations.

FIG. 7 shows the cumulative time (hours) for daily average of hydrophobicity when hydrophobicity>4, and paper machine runnability issues. 0=no runnability issues. 1=runnability issues.

Figure 8:
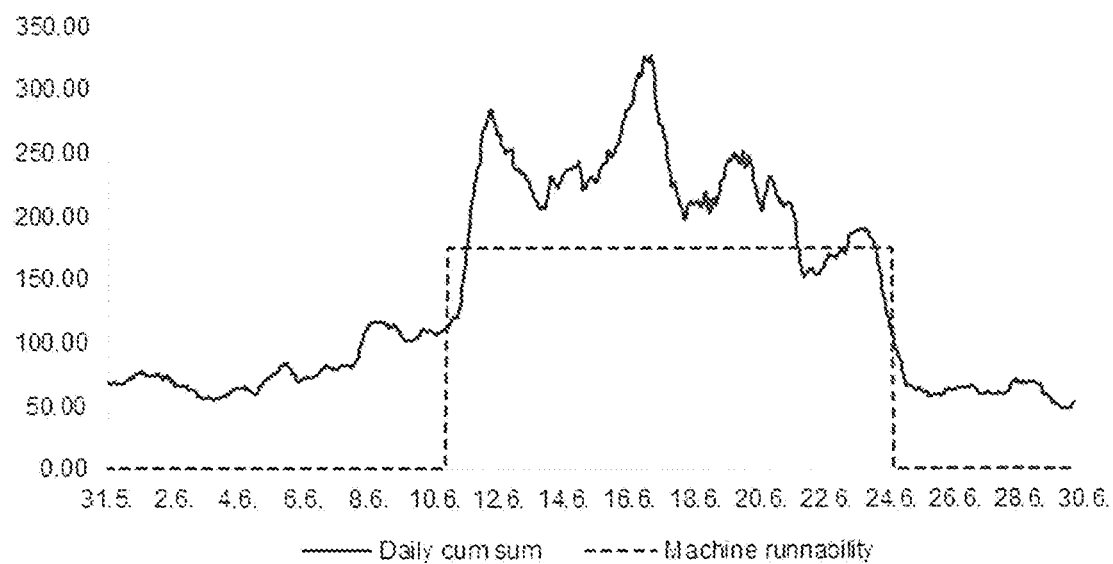

FIG. 8 shows the daily cumulative sum of hydrophobicity of colloids, and paper machine runnability issues. 0=no runnability issues. 1=runnability issues.

Two risk indicators were created.

Risk indicator 1 was cumulative time. If the cumulative time of hydrophobicity is 0, then the risk level is 0 (low). If the cumulative time is above 0 but less than 50 hours, then the risk level is 1 (medium). If the cumulative time>50 hours, then the risk level is 2 (high).

Risk indicator 2 was cumulative hydrophobicity. If the daily cumulative sum of hydrophobicity<90, then the risk level=0 (low). If the daily cumulative sum of hydrophobicity is above 90 but less than 125, then the risk for runnability issues increases (risk level=1, medium). If the daily cumulative sum of hydrophobicity is more than 125, then risk for runnability issues is very high (risk level=2, high).

Final risk levels for paper machine runnability issues were calculated on the basis of said two risk indicators such that predicted risk level=output of risk indicator 1+output of risk indicator 2. The predicted risk level was expressed in integer values from 0 to 4 where 0=low risk and 4=high risk.

Figure 9:
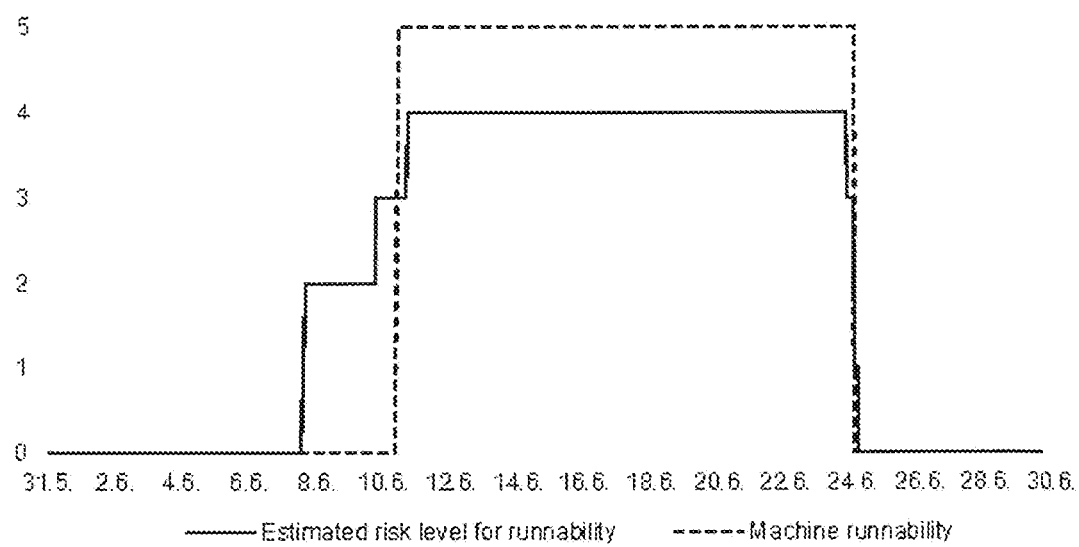

FIG. 9 shows predicted (estimated) risk levels as a function of time, and paper machine runnability issues. 0=no runnability issues. 1=runnability issues. As can be seen from FIG. 9, the predicted (estimated) risk level started to warn of the increased risk of runnability issues on 8 June, i.e. two days before there were significant deposit problems in the paper machine (starting from 10 June).

The inventive technology is generic and can be widely applied in the paper industry, including stickies control of recycled pulp and mechanical pulp treatment. It can be used for online monitoring of particle populations like colloids, fines, fillers, or agglomerates, and their hydrophobicity. The inventive online system enables real-time problem solving and optimization of chemistry in a paper mill.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

It will be obvious to a person skilled in the art that, as the technology advances, the inventive concept can be implemented in various ways. The invention and its embodiments are not limited to the examples described above but may vary within the scope of the claims.

The invention claimed is:

1. A method for estimating and/or predicting a runnability risk level and/or end product quality risk level for a pulp, board or papermaking process, the method comprising:
    providing samples from at least one aqueous stream of the pulp, board or papermaking process;
    measuring hydrophobicity values of at least two samples originating from a same aqueous stream of the pulp, board or papermaking process;
    producing a hydrophobicity measurement signal of measured hydrophobicity values as a function of time for said at least one aqueous stream;
    processing said hydrophobicity measurement signal to calculate a runnability risk level and/or end product quality risk level for the pulp, board or papermaking process, wherein the processing includes calculating at least one mathematical index, based at least:
        on the hydrophobicity measurement signal produced for said at least one aqueous stream, and
        optionally on an amount of particles in said at least one aqueous stream as a function of time, or another property of said at least one aqueous stream as a function of time, and/or on production data as a function of time,
    wherein the mathematical index and optionally the amount of the particles in said at least one aqueous stream as a function of time, the another property of said at least one aqueous stream as a function of time, and/or the production data as a function of time is used as a risk indicator input in calculating the runnability risk level and/or end product quality risk level; and
    based on the runnability risk level and/or end product quality risk level calculated for the pulp, board or papermaking process, indicating the runnability risk level and/or the end product quality risk level for the pulp, board or papermaking process.

2. A method for estimating or predicting a runnability risk level and/or end product quality risk level for a pulp, board or papermaking process, the method comprising:
    providing samples from at least one aqueous stream of the pulp, board or papermaking process;
    fractionating the samples into fractions based on mass and/or size of particles;
    measuring hydrophobicity values of fractions of at least two samples originating from a same aqueous stream;
    producing a hydrophobicity measurement signal of measured hydrophobicity values as a function of time for the fractions of said at least one aqueous stream;
    processing said hydrophobicity measurement signal to calculate a runnability risk level and/or end product quality risk level for the pulp, board or papermaking process, wherein the processing includes calculating at least one mathematical index, based at least:
        on the hydrophobicity measurement signal produced for the fractions of said at least one aqueous stream, and
        optionally on an amount of particles in said at least one aqueous stream as a function of time, on another property of said at least one aqueous stream as a function of time, and/or on production data as a function of time,
    wherein the mathematical index and optionally the amount of the particles in said at least one aqueous stream as a function of time, the another property of said at least one aqueous stream as a function of time and/or the production data as a function of time is used as a risk indicator input in calculating the runnability risk level and/or end product quality risk level; and
    based on the runnability risk level and/or end product quality risk level calculated for the pulp, board or papermaking process, indicating the runnability risk level and/or the end product quality risk level for the pulp, board or papermaking process.

3. A method as claimed in claim 2, wherein the method comprises:
    measuring hydrophobicity values of samples originating from at least two different aqueous streams of the pulp, board or papermaking process;
    producing a hydrophobicity measurement signal as a function of time for a difference between the hydrophobicity values measured for the at least two aqueous streams;
    processing said hydrophobicity measurement signal to calculate a runnability risk level and/or end product quality risk level for the pulp, board or papermaking process, wherein the processing includes calculating at least one mathematical index, based at least:
        on the hydrophobicity measurement signal produced for said at least two aqueous streams, and
        optionally on an amount of particles in said at least two aqueous streams as a function of time, on another property of said at least two aqueous streams as a function of time, and/or on production data as a function of time,
    wherein the calculated mathematical index and optionally the amount of the particles in said at least two aqueous streams as a function of time, the another property of said at least two aqueous streams as a function of time, and/or production data as a function of time is used as a risk indicator input in the calculation of the runnability risk level and/or end product quality risk level; and
    based on the runnability risk level and/or end product quality risk level calculated for the pulp, board or papermaking process, indicating the runnability risk level and/or the end product quality risk level for the pulp, board or papermaking process.

4. A method as claimed in claim 3, the method comprising:
    adding a hydrophobic dye to a sample or fraction thereof to stain the particles in the sample or fraction thereof; and
    measuring by optical measurement a fluorescence intensity value for the sample or fraction thereof to produce the hydrophobicity measurement signal, wherein the hydrophobicity measurement signal is representative of a hydrophobicity of the particles in the aqueous stream.

5. A method as claimed in claim 4, wherein:
    the calculated mathematical index includes a moving cumulative sum of the hydrophobicity values, cumulative time of the hydrophobicity values, moving median of the hydrophobicity values, moving maximum of the hydrophobicity values, and/or moving average of the hydrophobicity values.

6. A method as claimed in claim 4, wherein:
the calculated mathematical index includes a sum of measured hydrophobicity values during a selected time period, an average of the measured hydrophobicity values during a selected time period, a median of the measured hydrophobicity values during a selected time period, and/or a maximum of the measured hydrophobicity values during a selected time period.

7. A method as claimed in claim 4, wherein:
the calculated mathematical index includes a difference between consecutive averages of the measured hydrophobicity values during selected time periods,
the calculated mathematical index includes a difference between consecutive hydrophobicity values multiplied with a gain value, and/or
the calculated mathematical index includes the hydrophobicity measurement signal multiplied with a gain value.

8. A method as claimed in claim 2, the method comprising:
fractionating the sample into one or more of a fiber fraction, agglomerate fraction, floc fraction, fines fraction, and colloid fraction.

9. A method as claimed in claim 2, wherein said another property of the aqueous stream comprises:
one or more of pH, conductivity, charge, temperature, chemical oxygen demand, particle size, consistency, and/or ash consistency.

10. A method as claimed in claim 2, wherein calculating the risk level comprises:
inputting the risk indicator input to a risk indicator, the risk indicator comprising one or more of a mathematical model, equation, statistical model, regression analysis based model, and/or rule based model.

11. A method as claimed in claim 2, wherein calculating the risk level comprises:
inputting the risk indicator input to a risk indicator, wherein the risk indicator includes a threshold value for at least one risk indicator input and/or a weighting coefficient for at least one risk indicator input.

12. A method as claimed in claim 2, wherein the method comprises:
predicting runnability risks and/or end product quality risks caused by changes in process conditions of the pulp, board or papermaking process.

13. A method as claimed in claim 2, wherein the method comprises, based on the runnability risk level and/or the end product quality risk level:
controlling a concentration of hydrophobic contaminants in one or more aqueous streams of the pulp, board or papermaking process by:
manually and/or automatically adjusting the dosing of at least one chemical into the one or more aqueous streams of the pulp, board or papermaking process, and/or
manually and/or automatically adjusting a dosing of washing water into the one or more aqueous streams of the pulp, board or papermaking process.

14. A method as claimed in claim 2, comprising:
selecting or creating a risk indicator based on historical operational data on the pulp, board or papermaking process, and/or
a risk indicator which is process-specific.

15. A method as claimed in claim 2, wherein the method comprises:
outputting to a user the runnability risk level and/or the end product quality risk level.

16. A method as claimed in claim 2, wherein the method comprises:
indicating to a user, if the runnability risk level and/or the end product quality risk level exceeds a predefined value.

17. A method as claimed in claim 2, wherein the method comprises:
raising an alarm, if the runnability risk level and/or the end product quality risk level exceeds a predefined value.

18. A method as claimed in claim 2, wherein
a moving cumulative sum of the hydrophobicity is a daily cumulative sum for the hydrophobicity,
a cumulative time of the hydrophobicity is a time interval during which the hydrophobicity exceeds a predefined hydrophobicity value,
a moving median of the hydrophobicity is a daily median for the hydrophobicity, and/or
a moving average of the hydrophobicity is a daily average for the hydrophobicity.

19. The method according to claim 2, comprising:
monitoring and controlling of chemical performance in the pulp, board or papermaking process.

20. An apparatus for estimating or predicting a runnability risk level and/or end product quality risk level for a pulp, board or papermaking process, the apparatus comprising:
a sampler configured to obtain samples from at least one aqueous stream of a pulp, board or papermaking process;
a hydrophobicity meter configured to measure hydrophobicity values of at least two samples originating from a same aqueous stream of the pulp, board or papermaking process;
a processor configured to for producing a hydrophobicity measurement signal of measured hydrophobicity values as a function of time for said at least one aqueous stream;
wherein the processor is further configured to process said hydrophobicity measurement signal to calculate a runnability risk level and/or end product quality risk level for the pulp, board or papermaking process, by calculating at least one mathematical index based on:
the hydrophobicity measurement signal produced for said at least one aqueous stream, and
optionally an amount of particles in said at least one aqueous stream as a function of time, another property of said at least one aqueous stream as a function of time and/or production data as a function of time,
wherein the processor is further configured to:
use the calculated mathematical index, and optionally the amount of the particles in said at least one aqueous stream as a function of time, the another property of said at least one aqueous stream as a function of time, and/or the production data as a function of time, as a risk indicator input in calculating the runnability risk level and/or end product quality risk level, and
based on the risk level calculated for the pulp, board or papermaking process, indicate the runnability risk level and/or end product quality risk level for the pulp, board or papermaking process.

21. An apparatus for estimating or predicting a runnability risk level and/or end product quality risk level for a pulp, board or papermaking process, the apparatus comprising:

a sampler configured to obtain samples from at least one aqueous stream of the pulp, board or papermaking process;

a fractionator configured to fractionate the sample into fractions based on mass and/or size of particles;

a hydrophobicity meter configured to measure hydrophobicity values of fractions of at least two samples originating from a same aqueous stream;

a processor configured to produce a hydrophobicity measurement signal of measured hydrophobicity values as a function of time for the fractions of said at least one aqueous stream;

wherein said processor is further configured to process said hydrophobicity measurement signal to calculate a runnability risk level and/or end product quality risk level for the pulp, board or papermaking process, by calculating at least one mathematical index based at least:

on the hydrophobicity measurement signal produced for the fractions, and optionally on an amount of particles in said at least one aqueous stream as a function of time, another property of said at least one aqueous stream as a function of time, and/or production data as a function of time, wherein the processor is further configured to:

use the calculated mathematical index, and optionally the amount of the particles in said at least one aqueous stream as a function of time, the another property of said at least one aqueous stream as a function of time, and/or the production data as a function of time, as a risk indicator input in calculating the runnability risk level and/or end product quality risk level; and based on the risk level calculated for the pulp, board or papermaking process, indicate the runnability risk level and/or end product quality risk level for the pulp, board or papermaking process.

22. An apparatus as claimed in claim 21, wherein:

the hydrophobicity meter is configured to measure hydrophobicity values of samples originating from at least two different aqueous streams of the pulp, board or papermaking process;

the processor is further configured to produce a hydrophobicity measurement signal as a function of time for a difference between the hydrophobicity values measured for the at least two aqueous streams;

the processor being configured to process said hydrophobicity measurement signal to calculate a runnability risk level and/or end product quality risk level for the pulp, board or papermaking process, by calculating at least one mathematical index, based at least:

on the hydrophobicity measurement signal produced for said at least two aqueous streams, and optionally on the amount of particles in said at least two aqueous streams as a function of time, the another property of said at least two aqueous streams as a function of time, and/or the production data as a function of time, wherein the processor is configured to:

use the calculated mathematical index and optionally the amount of the particles in said at least two aqueous streams as a function of time, the another property of said at least two aqueous streams as a function of time, and/or the production data as a function of time as a risk indicator input in the calculation of the runnability risk level and/or end product quality risk level; and based on the runnability risk level and/or end product quality risk level calculated for the pulp, board or papermaking process, indicating the runnability risk level and/or the end product quality risk level for the pulp, board or papermaking process.

23. An apparatus as claimed in claim 22, wherein the processor is configured to:

calculate the risk level by inputting the risk indicator input to a risk indicator, the risk indicator being selected from one or more of a mathematical model, equation, statistical model, regression analysis based model, and rule based model.

24. An apparatus as claimed in claim 23, wherein the processor is configured to:

calculate the risk level by inputting the risk indicator input to a risk indicator, wherein the risk indicator includes a threshold value for at least one risk indicator input and/or a weighting coefficient for at least one risk indicator input.

25. An apparatus as claimed in claim 24, configured to predict runnability risks and/or end product quality risks caused by changes in process conditions of the pulp, board or papermaking process.

26. An apparatus as claimed in claim 25, configured to, based on the runnability risk level and/or the end product quality risk level:

control a concentration of hydrophobic contaminants in one or more aqueous streams of the pulp, board or papermaking process by:

manually and/or automatically adjusting a dosing of at least one chemical into the one or more aqueous streams of the pulp, board or papermaking process, and/or manually and/or automatically adjusting a dosing of washing water into the one or more aqueous streams of the pulp, board or papermaking process.

27. An apparatus as claimed in claim 26, configured to:

select or create a risk indicator based on historical operational data on the pulp, board or papermaking process, and/or a risk indicator which is process-specific.

28. An apparatus as claimed in claim 27, configured to:

output to a user the runnability risk level and/or the end product quality risk level.

29. An apparatus as claimed in claim 28, configured to:

indicate to a user, if the runnability risk level and/or the end product quality risk level exceeds a predefined value.

30. An apparatus as claimed in claim 29, configured to:

raise an alarm, if the runnability risk level and/or the end product quality risk level exceeds a predefined value.

* * * * *